United States Patent
Varasi et al.

[11] Patent Number: 5,973,006
[45] Date of Patent: Oct. 26, 1999

[54] FLUORO-SUBSTITUTED BENZOYLPROPIONIC ACID DERIVATIVES

[75] Inventors: Mario Varasi, Milan; Antonio Giordani, Pavia; Carmela Speciale, Nerviano; Massimo Cini, Lainate; Alberto Bianchetti, Milan, all of Italy

[73] Assignee: Pharmacia & Upjohn S.p.A., Milan, Italy

[21] Appl. No.: 09/051,486

[22] PCT Filed: Oct. 4, 1996

[86] PCT No.: PCT/EP96/04321

§ 371 Date: Apr. 20, 1998

§ 102(e) Date: Apr. 20, 1998

[87] PCT Pub. No.: WO97/15550

PCT Pub. Date: May 1, 1997

[30] Foreign Application Priority Data

Oct. 20, 1995 [GB] United Kingdom ............... 9521486

[51] Int. Cl.⁶ .......................... A01N 37/12; A01N 37/18; C07C 229/28; C07C 233/05
[52] U.S. Cl. .......................... 514/567; 514/541; 514/620; 560/38; 562/449; 564/164
[58] Field of Search ............... 562/449; 560/38; 564/164; 514/567, 541, 620

[56] References Cited

U.S. PATENT DOCUMENTS 5,519,055  5/1996  Schwarcz et al. .
5,708,030  1/1998  Schwarcz et al. .

FOREIGN PATENT DOCUMENTS

95/03271  2/1995  WIPO ................ C07C 229/36

*Primary Examiner*—Gary Geist
*Assistant Examiner*—Brian J. Davis
*Attorney, Agent, or Firm*—Oblon, Spivak, McClelland, Maier & Neustadt, P.C.

[57] ABSTRACT

A fluoro-substituted benzoylpropionic acid compound of formula (I) either as a single optical isomer or as a mixture of optical isomers

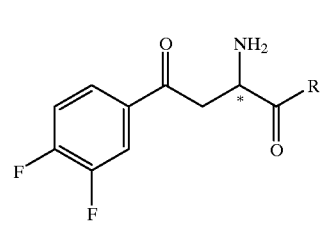

(I)

wherein

R is hydroxy, amino, hydroxylamine, —OR', —NHR', N(R')$_2$ or —NHOR' in which R' is C$_1$–C$_6$ alkyl or benzyl;

or a pharmaceutically acceptable salt thereof.

8 Claims, No Drawings

FLUORO-SUBSTITUTED BENZOYLPROPIONIC ACID DERIVATIVES

BACKGROUND OF THE INVENTION

1. Field of the Invention

The present invention relates to fluoro-substituted benzoylpropionic acid derivatives, to their pharmaceutically acceptable salts, to a process for their preparation and to pharmaceutical compositions comprising them.

2. Description of the Related Art

Our previous International patent application WO 95/03271 refers to 2-amino-4-phenyl-4-oxo-butyric acid derivatives of formula (IA) either as single isomers or as racemic mixture

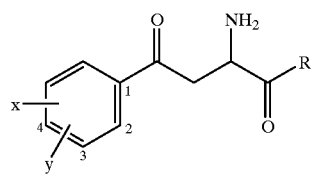

(IA)

and pharmaceutically acceptable salts thereof,
wherein
each of the groups X and Y is, independently, hydrogen, halogen, trifluoromethyl, hydroxy, $C_1$–$C_5$ alkyl, benzyl, $C_6$–$C_{10}$ aryl, OR', —SR', SOR', $SO_2R'$ in which R' is $C_1$–$C_5$ alkyl or benzyl; and R is hydroxy, OR', amino, NHR', —N(R')$_2$, hydroxylamine or —NHOR' in which R' is as defined above; provided that R is not hydroxy when:
  (i) X and Y are simultaneously hydrogen; or
  (ii) X and Y are in positions 3 and 4 of the phenyl ring and are simultaneously a hydroxy group or a —OR' group in which R' is methyl; or
  (iii) one of the X and Y groups is hydrogen and the other is in position 4 of the phenyl ring and is hydroxy, chlorine, fluorine, methyl, n-propyl or methoxy.

In WO 95/03271 the compounds of formula (IA) are described as effective in inhibiting the activity of the enzymes kynureninase and/or kynurenine-3-hydroxylase which are involved in the metabolic pathway of kynurenines leading to the formation of quinolinic acid, a tryptophan neurotoxic metabolite with excitatory activity in the mammalian central nervous system. The compounds of formula (IA) may therefore be employed in the prevention and/or treatment of a variety of nervous system diseases wherein the inhibition of the enzymes kynureninase or kynurenine-3-hydroxylase is needed; namely, they can be useful in the prevention and/or treatment of a nervous system disease related to a deranged production of quinolinic acid or excessive activation of neurotransmission mediated by N-methyl-D-aspartic acid.

For example, the compounds of formula (IA) may be useful in the prevention and/or treatment of neurodegenerative pathologies including, for example, Huntington's chorea, Alzheimer's disease, Parkinson's disease, dementia caused by acquired immunodeficiency syndrome (AIDS), multi-infarctual dementia, cerebral ischemia, cerebral hypoxia and epilepsy.

The compounds of formula (IA) are, in general, soluble in aqueous vehicles suitable for parenteral administration.

In accordance with the present invention, it has now been surprisingly found that certain fluoro-substituted benzoyl-propionic acid derivatives, which represent a selected class of compounds of formula (IA), not specifically disclosed in WO95/03271, possess excellent solubility. These novel fluoro derivatives, which are selective inhibitors of the enzyme Kynurenine-3-hydroxylase, are considerably more soluble than the corresponding di-chloro derivatives disclosed in WO 95/03271 and are therefore particularly useful for injectable administration purposes.

BRIEF SUMMARY OF THE INVENTION

Accordingly, the present invention provides an optically active or racemic substituted benzoylpropionic acid derivative of formula (I)

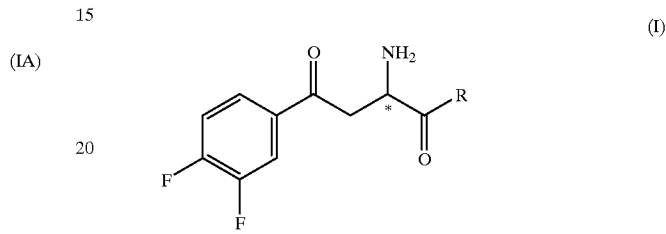

(I)

wherein
R is hydroxy, amino, hydroxylamine, —OR', —NHR', —N(R')$_2$ or —NHOR' in which R' is $C_1$–$C_6$ alkyl or benzyl; or a pharmaceutically acceptable salt thereof.

DETAILED DESCRIPTION OF THE INVENTION

The compounds of formula (I) possess an asymmetric carbon atom in the asterisked position and can therefore exist either as individual optical isomers or as racemic mixture.

The scope of the present invention encompasses both the individual optical isomers and the racemic mixture of the formula (I) compounds.

With reference to formula (I), the preferred meanings of the substituent R are hydroxy, amino, hydroxylamino or OR' in which R' is $C_1$–$C_6$ alkyl and benzyl.

The term $C_1$–$C_6$ alkyl includes, for example $C_1$–$C_4$ alkyl such as methyl, ethyl, n-propyl, isopropyl and n-butyl; preferably, it is methyl, ethyl or n-propyl.

The pharmaceutically acceptable salts of the compounds of formula (I) include both salts with pharmaceutically acceptable acids, either inorganic acids, such as, e.g., hydrochloric, hydrobromic, nitric or sulphuric acid or organic acids, such as, e.g., citric, tartaric, maleic, fumaric, methanesulfonic or ethanesulfonic acid, and salts with pharmaceutically acceptable bases, both inorganic bases such as, e.g., hydroxides of alkali metals, for example, sodium or potassium, or alkaline-earth metals such as, e.g., calcium, magnesium, zinc or aluminium, and organic bases, such as, e.g., aliphatic amines such as, e.g., methylamine, diethylamine, trimethylamine, ethylamine or heterocyclic amines such as, e.g., piperidine. Preferred salts according to the invention are hydrochlorides.

Specific examples of compounds of formula (I) according to this invention are the following:

(R,S)-2-amino-4-oxo-4-(3',4'-difluorophenyl)butanoic acid;

(R)-2-amino-4-oxo-4-(3'-4'-difluorophenyl)butanoic acid;

(S)-2-amino-4-oxo-4-(3'-4'-difluorophenyl)butanoic acid; and their pharmaceutically acceptable salts.

A compound of formula (I) may be prepared by a process which comprises:

a) reacting a compound of formula (II)

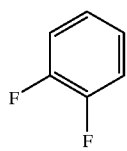

(II)

with a compound of formula (III) either as a single (R) or (S) enantiomer or as racemic mixture

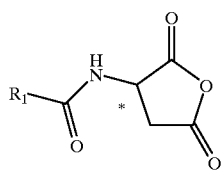

(III)

wherein $R_1$ is hydrogen, methyl, trifluoromethyl, $C_1$–$C_6$ alkoxy or benzyloxy, to obtain a compound of formula (IV) either as a single (R) or (S) enantiomer or as racemic mixture

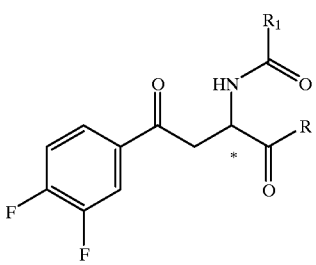

(IV)

wherein $R_1$ is as defined above;

b) converting a compound of formula (IV) either as a single (R) or (S) enantiomer or as racemic mixture into a single (R) or (S) enantiomer or racemic mixture of a compound of formula (I) wherein R is hydroxy, and, if desired, converting a compound of formula (I) wherein R is hydroxy into a compound of formula (I) wherein R is other than hydroxy.

Preferably, $R_1$ in the above formulae (III) and (IV) is trifluoromethyl, methoxy or ethoxy.

The reaction of a compound of formula (II) with a compound of formula (III), as described under step a), may be carried out according to known methods (see, for example, J. E. Nordlander, J. Org. Chem., 50, 3619–22, 1985 and D. G. Melillo, J. Org. Chem. 52, 5143–50, 1987); for example, the reaction may be performed in the presence of a suitable Lewis acid catalyst, in an inert solvent such as, e.g., dichloromethane or dichloroethane typically dichloromethane or in a suitable aromatic hydroxycarbon such as, e.g., chlorobenzene, benzene, nitrobenzene or a mixture of such solvents, at a temperature ranging from about −5° C. to about 60° C.; optionally in the presence of a cosolvent such as, for example, nitromethane.

A suitable Lewis acid may be, e.g., anhydrous aluminium trichoride, anhydrous tin dichloride, titanium tetrachloride or zinc dichloride, typically aluminium trichloride.

The conversion of a compound of formula (IV) into a compound of formula (I) as described under step b) may be carried out according to known procedures under either acidic or alkaline hydrolytic conditions.

Alkaline hydrolysis may be performed by an alkali metal hydroxide such as, e.g., lithium, sodium or potassium hydroxide or sodium carbonate, in a suitable solvent such as, e.g., aqueous methanol or ethanol, at a temperature ranging from about 0° C. to about 50° C.

Acid hydrolysis may be carried out by a halogenidric acid such as, e.g., hydrochloric or hydrobromic acid, at a temperature ranging from about 60° C. to about 110° C. for a time which may vary from about 4 hours to about 12 hours.

The optional conversion of a compound of formula (I) wherein R is hydroxy into another compound of formula (I) wherein R is other than hydroxy may be carried out following known procedures.

The compounds of formula (II) and (III) are known compounds or may be obtained by known procedures.

The compounds of formula (I) are active as kynurenine-3-hydroxylase enzyme inhibitors and they can be useful in the prevention and/or treatment of a neurodegenerative disease wherein the inhibition of such an enzyme is needed.

They can therefore be useful, e.g., in the prevention and/or treatment of a variety of nervous system diseases related to a deranged production of quinolinic acid or excessive activation of neurotransmission mediated by N-methyl-D-aspartic acid, such as, e.g., neurodegenerative pathologies including, e.g., Huntington's chorea, Alzheimer's disease, Parkinson's disease, dementia caused by acquired immunodeficiency syndrome (AIDS), multi infarctual dementia, cerebral ischemia, cerebral hipoxia and epilepsy.

A human or animal may thus be treated by a method which comprises the administration thereto of a pharmaceutically effective amount of a compound of formula (I) or salt thereof.

The condition of the human or animal can thereby be improved.

The efficacy of the compounds of the invention in the inhibition of the enzyme kynurenine-3-hydroxylase has been evaluated both in rat brain homogenate and in rat liver, determining the conversion of L-kynurenine to L-3-hydroxy-kynurenine according to the methods described below.

Kynurenine-3-hydroxylase Assay in the Rat Brain

Brain was homogenized in ice-cold 0.32 M sucrose and centrifuged at 12000×g for 30 min at 4° C. The pellet was washed three times with 0.32 M sucrose by centrifugation and suspended in 0.14 M KCl in 20 mM K-phosphate buffer at pH 7 (1 g tissue in 2 ml buffer). The reaction mixture contained: 75 µl of suspended homogenate; 100 µl of substrate solution containing 50 mM K-phosphate buffer pH 7.5, 2 MM $MgCl_2$, 0.4 mM NADPH, and 50 µM L-kynurenine (final concentration), and 25 µl of different concentrations of inhibitor solutions. The reaction was stopped by addition of 200 µl of 1 M $HClO_4$ after 60 min incubation. L-3-hydroxykynurenine formed was quantified by HPLC with coulometric detection at a working voltage of +0.2 V. The column was a 10 cm $C_{18}$ reversed phase (3 µm. The mobile phase consisted of 950 ml distilled water, 20 ml acetonitrile, 9 ml triethylamine, 5.9 ml phosphoric acid, 100 mg sodium EDTA and 1.5 g heptanesulfonic acid. The flow rate was 1 ml/min.

Kynurenine-3-hydroxylase Assay in the Rat Liver

The efficacy of the compounds of formula (I) in the inhibition of the enzyme kynurenine-3-hydroxylase has been evaluated in rat liver mitochondrial extract as reported below, according to known methods (A Radiometric Assay for Kynurenine 3-Hydroxylase Based on the Release of $^3H_2O$ during Hydroxylation of L-(3,5-$^3$H)Kynurenine; Joel B. Erickson, Ellen M. Flanagan, Suzanne Russo, and John F. Reinhard. Jr.; Analytical Biochem. (1992), 205, 257–262) with minor modifications.

The assay for kynurenine 3-hydroxylase was based on the enzymatic synthesis of tritiated water during the hydroxylation reaction. Radiolabeled water was quantified following selective adsorption of the isotopic substrate and its metabolite with activated charcoal.

Rat liver mitochondrial extract was used as enzymatic preparation for this assay.

The assay for kynurenine 3-hydroxylase activity was carried out at 37° C. for a time of 30 min. The reaction mixture of a total volume of 100 ml was constituted of 44 mg of suspended extract, 100 mM Tris/Cl buffer pH 8.1, 10 mM EDTA, 100 mM KCl, 0.8 mM NADPH, 0.025 mM L-kynurenine, 0.5 mCi L-(3,5-$^3$H)Kynurenine (10 Ci/mmol) and 10 ml of different concentration of inhibitor solutions. After the incubation the reaction was terminated by the addition of 1 mL of 7.5% (w/v) activated charcoal, vortexed and centrifugated for 7 min.

A 500 ml aliquot of supernatant was counted by scintillation spectroscopy in 5 ml of liquid scintillation.

As an example, the compounds of the present invention:
(R,S)-2-amino-4-(3',4'-difluorophenyl)-4-oxo-2-butanoic acid hydrochloride (internal code: PNU 156830);
(S)-2-amino-4-(3',4'-difluorophenyl)-4-oxo-2-butanoic acid hydrochloride (internal code: PNU 158393); and
(R)-2-amino-4-(3',4'-difluorophenyl)-4-oxo-2-butanoic acid hydrochloride (internal code: PNU 158392) have been tested according to the methods described above.

The obtained results are reported in the following Table 1.

TABLE 1

| Enzyme Inhibition Compound | (Brain) $IC_{50}$ ($\mu$M) | (Liver) $IC_{50}$ ($\mu$M) |
|---|---|---|
| PNU 156830 | 0.12 | 0.42 |
| PNU 158393 | — | 0.22 |
| PNU 158392 | — | 10.9 |

The tested compounds were found to be significantly active in inhibiting the enzyme kynurenine-3-hydroxylase.

The following Table 2 reports the solubility in water at the indicated pH of a representative compound of the invention (R,S)-2-amino-4-(3',4'-difluorophenyl)-4-oxo-2-butanoic acid hydrochloride (PNU 156830) in comparison with the known reference compound of WO 95/03271: (R,S)-2-amino-4-(3',4'-dichlorophenyl)-4-oxo-butanoic acid hydrochloride (internal code: PNU 156561).

TABLE 2

| | Solubility (mg/mL) | | |
|---|---|---|---|
| Compound | pH = 7.4 | pH = 8 | pH = 3 |
| PNU 156830 | 18 | 36 | 38 |
| PNU 156561 | 0.2 | 15 | — |

The data in Table 2 clearly show that the tested compound of the invention is surprisingly more soluble than the reference compound.

The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion; topically, e.g. in the form of creams. Preferably they are administered by oral or parenteral route, more preferably by oral route. The dosage depends on the age, weight, conditions of the patient and administration route. For example, a suitable dosage for oral administration to adult humans may be from 1 mg to 1000 mg per kg per day, preferably from 50 mg to 400 mg per kg.

The present invention includes in its scope also pharmaceutical compositions comprising an optically active or a racemic compound of formula (I), or a pharmaceutically acceptable salt thereof, in admixture with a pharmaceutically acceptable non-toxic carrier and/or diluent.

The pharmaceutical compositions containing the compounds of the invention are usually prepared following conventional methods and may be administered in a pharmaceutically suitable form.

Example of pharmaceutically suitable preparations can be found in the specification of WO 95/03271.

The following examples illustrate but do not limit the invention.

EXAMPLE 1

(R,S)-N-trifluoroacetyl-2-amino-4-oxo-4-(3',4'-difluorophenyl) Butanoic Acid

To an ice-cooled solution of 1,2-difluorobenzene (10 ml; 90 mmol) in dry dichloromethane (50 ml), (R,S)-N-trifluoroacetylaspartic anhydride (4 g; 20 mmol) was added in one portion. To the resulting solution, anhydrous aluminium trichloride (8 g.; 60 mmol) was slowly added portionwise, under vigorous stirring and dry nitrogen atmosphere, maintaining the temperature below 10° C. The so obtained deep-yellow suspension was stirred at 60° C. for 6 hrs.

The resulting reaction mixture was then poured into ice (200 g), and extracted with dichlorometane (3×50 ml), the collected organic extracts were washed with brine (2×10 ml), dried ($Na_2SO_4$), and evaporated in vacuum to afford the crude product (7.3 g) as an oily material. Recrystallization from hexane/ethyl ether afforded the pure titled compound as colourless prisms (5 g; 76%), m.p. 159–160° C.

$^1$H-NMR($d_6$-DMSO)ppm: 3.58 (d,2H);4.78 (m,1H); 7.60–8.10 (m,3H); 9.70 (d,1H), 13.20 (broad s,1H) MS (EI): 325 (M$^+$; 4.5), 307 (55.3), 210 (50), 141 (100) Microanalysis: calcd. for $C_{12}H_8F_5NO_4$: C 44.35; H 2.45; N 4.35. found: 44.52; 2.61; 4.08

(R,S)-2-amino-4-oxo-4-(3',4'-difluorophenyl)butanoic acid hydrochloride.

(R,S)-N-trifluoroacetyl-2-amino-4-oxo-4-(3',4'-difluorophenyl) butanoic acid (3 g ; 9.2 mmol) was dissolved in glacial acetic acid (30 ml); to the resulting solution warmed at 80° C., 6N hydrochloric acid (30 ml) was added on stirring and the reaction mixture was then warmed at 80° C. for 3 hrs.

In vacuum evaporation provided a colourless solid which was crystallised from ethyl acetate/ethanol; the pure titled compound slowly precipitated on standing at room temperature as colourless needles (1.9; 79%). m.p.: 175–176° C.

$^1$H-NMR($d_6$-DMSO) ppm: 3.78(d , 2H), 4.30 (t,1H), 7.60–8.10 (m, 3H), 8.10–9.10 (broad s, 3H) MS (FAB$^+$):

230.4 (M+H⁺) Microanalysis: calcd. for $C_{10}H_{10}F_2ClNO_3$: C45.24; H3.42; N5.27;Cl 13.37 found 45.08; 3.89; 5.15; 12.87

EXAMPLE 2

(S)-N-trifluoroacetyl-2-amino-4-oxo-4-(3',4'-difluorophenyl) Butanoic Acid

To an ice-cooled solution of 1,2-difluorobenzene (25 ml; 0.256 mol) in dry dichloromethane (170 ml), (S)-N-trifluoroacetylaspartic anhydride (12 g.; 0.054 mol) was added in one portion. To the resulting solution, anhydrous aluminium trichloride (21.5 g; 0.16 mol.) was slowly added portionwise, under vigorous stirring and dry nitrogen atmosphere, maintaining the temperature below 10° C. The so obtained deep-yellow suspension was stirred at room temperature for 3 hrs. and then at 50° C. for 5 hrs. The resulting reaction mixture was then poured into ice (400 g), and extracted with dichlorometane (3×100 ml), the collected organic extracts were washed with brine (2×50 ml ), dried ($Na_2SO_4$), and evaporated in vacuum to afford the crude product (7.3 g) as an oily material. Recrystallisation from hexane/ethyl ether afforded the pure titled compound as colourless prisms (8 g; 47%), m.p. 136°–137° C.

$[\alpha]_D$=+9.79° (c=0.9; 95% EtOH) ¹H-NMR(d₆DMSO, ppm): 3.58 (d,2H); 4.78(m,1H); 7.60–8.10(m,3H); 9.70 (d, 1H), 13.10 ( broad s, 1H) MS (EI): 325 (M⁺), 141.0 (100) Microanalysis: calcd. for $C_{12}H_8F_5NO_4$: C 44.35 ; H 2.45; N 4.35. found: 44.20; 2.43; 4.34

Following analogous procedures, (R)-N-trifluoroacetyl-2-amino-4-oxo-4-(3',4'-difluorophenyl) butanoic acid was obtained in 50% yield, starting from (R)-N-trifluoacetylaspartic anhydride. m.p. 136–137° C.

$[\alpha]_D$=+11.4° (c=0.7; 95% EtOH) ¹H-NMR(d₆-DMSO) ppm: 3.58(d,2H); 4.78(m,1H); 7.60–8.10(m,3H); 9.70 (d, 1H), 13.10 (broad s, 1H) MS: 325 (M⁺), 141.0 (100) Microanalysis: calcd. for $C_{12}H_8F_5NO_4$: C44.35; H 2.45; N 4.35. found: 44.43; 2.55; 4.29

(S)-2-amino-4-oxo-4-(3',4'-difluorophenyl)butanoic acid hydrochloride (S)-N-trifluoroacetyl-2-amino-4-oxo-4-(3',4'-difluorophenyl)butanoic acid (4 g; 12.3 mmol) was dissolved in glacial acetic acid (40 ml), to the resulting solution warmed at 80° C., 6N hydrochloric acid (40 ml) was added on stirring and the reaction mixture was further warmed at 80° C. for 3 hrs.

In vacuum evaporation provided a colourless solid which was crystallised from ethyl acetate/ethanol; the pure titled compound slowly precipitated on standing at room temperature as colourless needles (3.5 g; 80%). m.p.: 195–196° C.

$[\alpha]_D$=+33.3° (c=1; 95% EtOH) ¹H-NMR (d₆-DMSO) ppm: 3.78 (d,2H), 4.30 (t,1H), 7.60–8.10 (m,3H), 8.10–9.10 (broad s, 3H) MS: MS(FAB⁺): 230.4 (M+H⁺) Microanalysis:calcd. for $C_{10}H_{10}F_2ClNO_3$:C45.24; H3.42; N5.27;Cl 13.37 found: 45.08; 3.89; 5.35; 12.80

Following analogous procedure (R)-2-amino-4-oxo-4-(3', 4'-difluoro-phenyl)butanoic acid hydrochloride was obtained in 75% yield, starting from (R)-N-trifluoroacetyl-2-amino-4-oxo-4-(3',4'-difluorophenyl)butanoic acid m.p.: 195° C.

$[\alpha]_D$=−34.3° (c=1; 95% EtOH) Microanalysis:calcd. for$C_{10}H_{10}F_2ClNO_3$:C45.24; H3.42; N5.27; Cl 13.37 found: 42.63; 4.30; 4.97; 12.73 DSC 10° C./min.: solvent lost 55–95° C. TGA 1° C./min.: solvent lost (3.8%) 35–75° C.

EXAMPLE 3

Capsule, each weighing 0.230 g and containing 50 mg of the active substance can be prepared as follows:

Composition for 500 capsules:

| | |
|---|---|
| (R,S)-2-amino-4-(3',4'-difluorophenyl)-4-oxo-butyric acid | 25 g |
| Lactose | 80 g |
| Corn starch | 5 g |
| Magnesium stearate | 5 g |

This formulation can be incapsulated in two hard gelating capsules of two pieces each with each capsule weighing 0.230 g.

EXAMPLE 4

Intramuscular Injection of 50 mg/ml

A pharmaceutical injectable composition can be manufactured dissolving 50 g of (R,S)-2-amino-4-(3'-4'-difluorophenyl)-4-oxo-butyric acid. HCl in sterile propyleneglycol (1000 ml) and sealed in 1–5 ml ampoules.

We claim:

1. A fluoro-substituted benzoylpropionic acid compound of formula (I) either as a single optical isomer or as a mixture of isomers

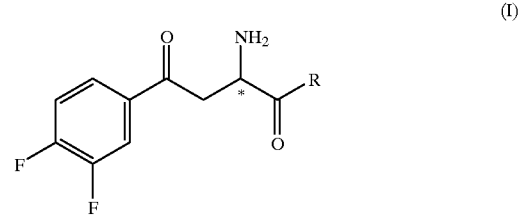

(I)

wherein

R is hydroxy, amino, hydroxylamine, —OR', —NHR', N(R')₂ or —NHOR' in which R' is $C_1$–$C_6$ alkyl or benzyl;

or a pharmaceutically acceptable salt thereof.

2. A compound selected from the group consisting of:

(R,S)-2-amino-4-(3',4'-difluorophenyl)-4-oxo-butyric acid, (R)-2-amino-4-oxo-4-(3'-4'-difluorophenyl) butanoic acid; and (S)-2-amino-4-oxo-4-(3'-4'-difluorophenyl)butanoic acid;

either as a single optical isomer or as a mixture thereof or a pharmaceutically acceptable salt thereof.

3. A pharmaceutically acceptable salt of a compound as claimed in claim 1 which is a hydrochloride salt.

4. A pharmaceutical composition which comprises, as an active ingredient, a compound as defined in claim 1 or a pharmaceutically acceptable salt thereof in admixture with a pharmaceutically acceptable diluent and/or carrier.

5. A method for treatment of a neurodegenerative disease in which inhibition of the enzyme kynurenine-3-hydroxylase is indicated comprising:

administering an effective amount of a compound of claim 1.

6. A method for treatment of a nervous system disease related to a deranged production of quinolinic acid or an excessive activation of neurotransmission mediated by N-methyl-D-aspartic acid comprising:

administering an effective amount of a compound of claim 1.

7. The method of claim 6, wherein the nervous system disease is a neurodegenerative disease.

8. The method of claim 7, wherein the neurodegenerative disease is selected from Huntington's chorea, Alzheimer's disease, Parkinson's disease, dementia caused by acquired immunodeficiency syndrome (AIDS), multi infarctual dementia, cerebral ischemia, cerebral ipoxia and epilepsy.

* * * * *